United States Patent
Laghi

(10) Patent No.: US 6,702,860 B1
(45) Date of Patent: Mar. 9, 2004

(54) DYNAMIC PROSTHETIC FOOT WITH MULTIPLE LOAD POINTS ON UPPER SECTION AND SOLE

(76) Inventor: Aldo A. Laghi, 14410 Eagle Point Dr., Clearwater, FL (US) 33762

( * ) Notice: Subject to any disclaimer, the term of this patent is extended or adjusted under 35 U.S.C. 154(b) by 0 days.

(21) Appl. No.: 10/064,838

(22) Filed: Aug. 22, 2002

(51) Int. Cl.[7] .................................. A61F 2/66
(52) U.S. Cl. .......................... 623/55; 623/47
(58) Field of Search .............. 623/47, 50, 52, 623/53, 55, 27, 33, 35

(56) References Cited

U.S. PATENT DOCUMENTS

| | | | |
|---|---|---|---|
| 5,258,038 A | * 11/1993 | Robinson et al. | 623/49 |
| 5,314,499 A | * 5/1994 | Collier, Jr. | 623/47 |
| 5,728,177 A | * 3/1998 | Phillips | 623/55 |
| 5,944,760 A | * 8/1999 | Christensen | 623/55 |
| 6,071,313 A | * 6/2000 | Phillips | 623/55 |
| 6,165,227 A | * 12/2000 | Phillips | 623/53 |
| 6,197,068 B1 | * 3/2001 | Christensen | 623/55 |
| 2002/0013628 A1 | * 1/2002 | Harris | 623/55 |
| 2003/0009238 A1 | * 1/2003 | Whayne | 623/32 |

* cited by examiner

*Primary Examiner*—Corrine McDermott
*Assistant Examiner*—Thomas J Sweet
(74) *Attorney, Agent, or Firm*—Smith & Hopen, P.A.; Ronald E. Smith

(57) ABSTRACT

A dynamic prosthetic foot having multiple load points includes a sole having a toe end and a heel end. A longitudinally—extending slot divides the heel end of the sole into a lateral heel member and a medial heel member which respectively include a lateral, posterior pylon support and a medial, anterior pylon support. A heel end of the lateral heel member has a gradual ninety degree bend formed in so that it forms the lateral, posterior pylon support which is disposed normal to the sole. The medial heel member includes a return bend and a gradual ninety degree bend that positions the medial, anterior pylon support in anterior relation to the lateral, posterior pylon support. A heel extension is formed integrally with the lateral side only of the sole and diverges from the lateral, posterior pylon support along a transverse parting line.

13 Claims, 4 Drawing Sheets

DYNAMIC PROSTHETIC FOOT WITH MULTIPLE LOAD POINTS ON UPPER SECTION AND SOLE

BACKGROUND OF INVENTION

1. Field of the Invention

This invention relates, generally, to the art of prosthetics. More particularly, it relates to improvements in prosthetic feet.

2. Description of the Prior Art

During normal ambulation, the first part of a foot to contact the ground is the free end of the heel. This initial contact between heel and ground is known as the "heel strike." The free end of the heel is soft and thus cushions the heel strike to at least some extent. The hard bottom of the heel is the next part of the foot to strike the ground; its hardness allows it to support the entire weight of the body. The foot continues to rotate in the well-known way until the toes "push off" at the end of a step.

Early prosthetic feet were quite rigid and provided little or no cushion to the impact on the ground at the moment of "heel strike" and little or no elastic response at "push off." The shock of impact was thus transmitted directly to the skeletal structure of the user, and the lack of elastic response forced an unnatural gait.

Perhaps the earliest prosthetic foot that provided an elastic response at heel strike and push off is disclosed in U.S. Pat. No. 4,547,913 to Phillips, assigned to Flex Foot, Inc. Multiple versions of that device have been developed. The original version is formed of a carbon fiber epoxy matrix consisting of a one-piece combination pylon upper and a one-piece sole. Mechanical fasteners interconnect the upper and the sole. In a second embodiment, the pylon is a round hollow tube and is connected by mechanical fasteners to a rectangular-shaped upper. A third version is like the first except that a standard Sach® foot adapter is employed to connect a standard prosthetic pylon. A fourth version is like the third but has a slightly different geometry. In a fifth version, an elastomeric glue connects the upper and the sole. In additional embodiments, leaf springs or hydraulic cylinders are incorporated into the prosthetic foot.

Although the developments in the art since the mid 1980s have significantly advanced the technology of prosthetic feet, the known prosthetic feet still provide little or no heel elasticity in a direction parallel to the ground. Instead, they provide elastic response in a vertical plane. Thus, although the impact at heel strike is reduced vis a vis the pre-1980's prosthetic feet, the reduced impact is transmitted vertically to the skeletal structure of the user, and the elastic response in a vertical plane causes a four to six millimeter bounce at heel strike. This vertical response causes an unnatural walk because a healthy human heel is soft at the back or free end where heel strike occurs and is hard on the bottom so that it can support the entire weight of the body. Thus, the normal gait of a human includes a rolling motion as the back of the heel strikes the ground; there is no vertical motion causing the heel to bounce upon ground impact. Accordingly, there remains a need for a prosthetic foot that provides substantial heel elasticity in a direction parallel to the ground.

A healthy human foot rolls on the lateral part of the foot during ambulation. The medial part of the foot provides a cushion and the force required at push off. Thus, there is a smooth transition from heel strike to push off, with no vertical dynamic response of the type that could cause the foot to bounce. Prosthetic feet, however, do not provide a smooth transition from heel strike to push off. This lack of a smooth transition produces what is known in the industry as a "flat spot." The presence of a flat spot between heel strike and push off produces an unnatural gait.

More particularly, the dynamic response is primarily vertical at the heel and the toe of a prosthetic foot. There is little or no component of the dynamic response in a horizontal plane as present in a healthy natural foot. The absence of dynamic response in a horizontal plane results in a step like motion going from an elastic vertical motion at heel strike to little or no support at mid-stance (the flat spot), and then again to an elastic vertical motion at push off.

There is a need, therefore, for a prosthetic foot having a dynamic response in a horizontal plane during heel strike, that provides a smooth transition between heel strike and push off to eliminate the flat spot, and that provides a dynamic response in a horizontal plane during push off.

The human foot provides a more rigid support laterally than medially. This design is advantageous because when an instability occurs, the weight of the person shifts from the rigid outer or lateral edge of the foot to the less rigid inner or medial edge. In this way, the prosthetic foot takes advantage of the presence of the natural foot, i.e., the lateral-to-medial motion experienced at the moment of an instability shifts additional support duties to the natural foot. One major drawback of the heretofore known prosthetic feet is the fact that such feet provide an exactly vertical response during ambulation with no component toward the medial section of the foot. Thus, if an instability in one foot urges the person to fall away from the natural foot, there is no shift of weight toward the medial part of the prosthetic foot as would occur in a natural foot, and the likelihood of a fall is substantially increased.

A prosthetic foot is therefore needed that has differentiated medial and lateral stiffness so that it can respond to instabilities in much the same way as a natural foot.

However, in view of the prior art considered as a whole at the time the present invention was made, it was not obvious to those of ordinary skill in the pertinent art how the identified needs could be fulfilled.

SUMMARY OF INVENTION

The long-standing but heretofore unfulfilled need for a dynamic prosthetic foot is now met by a new, useful, and nonobvious dynamic prosthetic foot that provides multiple load points. The novel foot includes a sole having a toe end and a heel end. A slot is formed in the heel end and is substantially coincident with a longitudinal axis of the dynamic prosthetic foot. The slot extends from the heel end of the sole to a preselected point in the sole.

The slot divides the heel end into a lateral heel member and a medial heel member. A pair of pylon supports are formed in the heel end and are separated from one another by the slot. The pair of pylon supports includes a lateral, posterior pylon support and a medial, anterior pylon support.

A heel extension forms a part of the lateral heel member and is integral and generally coplanar with a lateral side only of the sole. The lateral, posterior pylon support diverges from the heel extension along a preselected transverse line about mid-length of the lateral side of the sole.

The lateral heel member includes a gradual ninety degree bend formed in the sole. The gradual ninety degree bend terminates in a vertical part that forms the lateral, posterior pylon support. The lateral, posterior pylon support is disposed substantially perpendicular to the sole.

The medial heel member includes a return bend formed in the sole at the heel end thereof. The medial heel member further includes a straight section substantially parallel to the sole that extends toward the toe of the prosthetic foot. The straight section terminates in a gradual ninety degree bend formed integrally with the straight section and the gradual ninety degree bend terminates in a vertical part that forms the medial, anterior pylon support. The medial, anterior pylon support is also disposed normal to the sole.

The straight section has a length sufficient to position the medial, anterior pylon support in leading, anterior relation to the lateral, posterior pylon support.

The sole has a first convexity formed in the heel end that performs the function of the bottom of a natural heel. The sole has a concavity, performing the function of a natural arch, that is longitudinally spaced from the first convexity. A second convexity that performs the function of the ball of a natural foot is longitudinally spaced from the concavity.

The slot that divides the heel into a lateral heel member and a medial heel member may also be described as extending about to the bight of the concavity that performs the function performed by the arch of a natural foot.

A lateral, posterior pylon connector adapted to receive a lateral, posterior pylon of a prosthetic leg is secured to a trailing end of the lateral, posterior pylon support. A medial, anterior pylon connector adapted to receive a medial, anterior pylon of a prosthetic leg is secured to a trailing end of the medial, anterior pylon support.

Forces acting on the lateral, posterior pylon connector are substantially confined to the lateral, posterior pylon support and forces acting on the medial, anterior pylon connector are substantially confined to the medial, anterior pylon support. Moreover, forces acting on the lateral, posterior pylon connector are similar to the forces acting on a fibula of a natural leg and forces acting on the medial, anterior pylon connector are similar to the forces acting on a tibia of a natural leg.

The lateral, posterior pylon support has a greater thickness than the medial, anterior pylon support. The greater thickness imparts greater strength and less flexibility so that forces applied to the lateral, posterior pylon support and the medial, anterior pylon support are transferred more to the medial, anterior pylon support than to the lateral, posterior pylon support, thereby mimicking the reaction of a natural foot to forces applied thereto.

In a second embodiment, each pylon support is elongated and serves as a pylon. This eliminates the need for a pylon connector attached to the back of the pylon supports of the first embodiment. In the second embodiment, each pylon is about twenty inches (20") in height and is cut to size as needed by a prosthetist at the time of fitting.

An important object of this invention is to provide a prosthetic foot having heel elasticity in a direction parallel to the ground.

Another important object is to provide a prosthetic foot having a smooth transition from heel strike to mid stance to push off.

Yet another object is to provide a prosthetic foot having differentiated medial and lateral stiffness so that an instability tends to shift weight from the lateral edge of the prosthetic foot to the medial edge thereof, just as in a natural foot.

Another important object is to provide a prosthetic foot having a heel divided into a lateral part and a medial part and where the flexing of the medial part exceeds the flexing of the lateral part.

These and other important objects, advantages, and features of the invention will become clear as this description proceeds.

The invention accordingly comprises the features of construction, combination of elements, and arrangement of parts that will be exemplified in the description set forth hereinafter and the scope of the invention will be indicated in the claims.

BRIEF DESCRIPTION OF DRAWINGS

For a fuller understanding of the nature and objects of the invention, reference should be made to the following detailed description, taken in connection with the accompanying drawings, in which.

DETAILED DESCRIPTION

Figure 1:
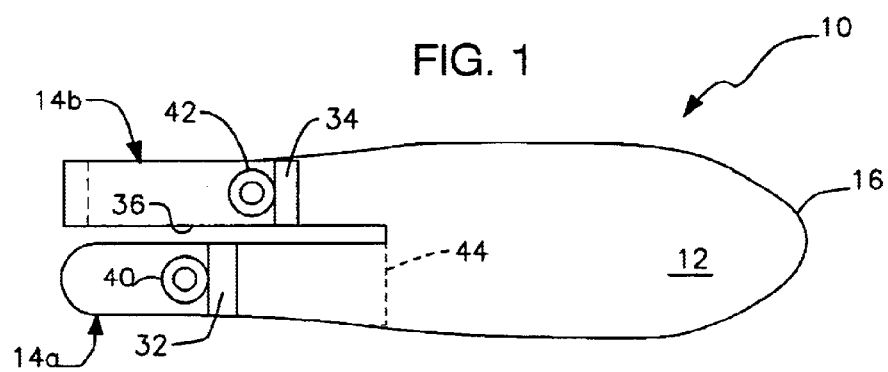
FIG. 1 is a top plan view of a first embodiment of a prosthetic foot with multiple load points having an upper section and sole.
Figure 2:
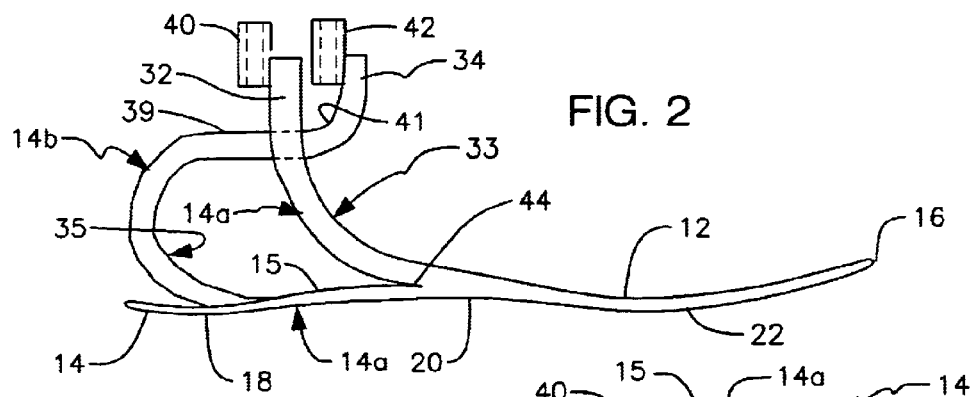
FIG. 2 is a side elevational view thereof.
Figure 3:
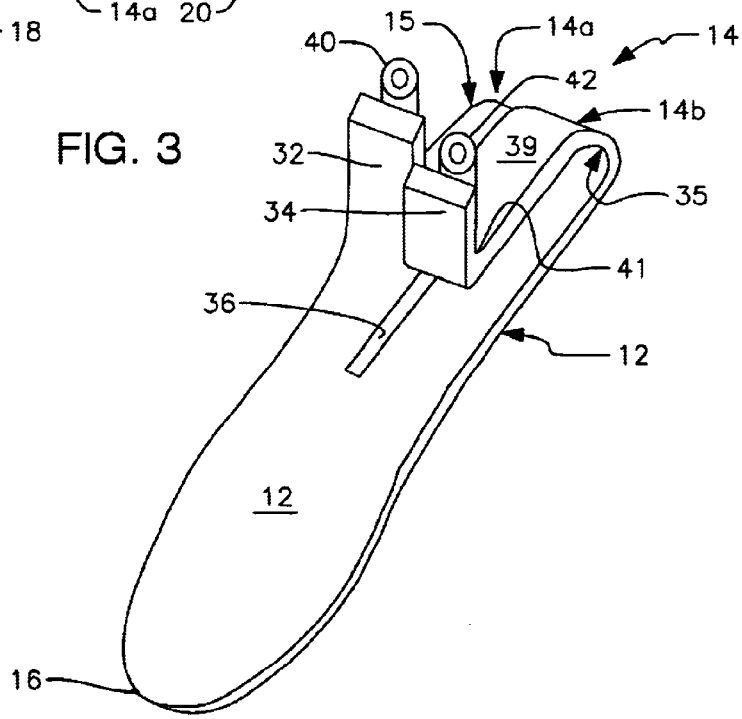
FIG. 3 is a perspective view thereof.

Referring to FIGS. 1–3, it will there be seen that the reference numeral 10 denotes an illustrative embodiment of the novel prosthetic foot having multiple load points with an upper section and a sole.

Prosthetic foot 10 includes a sole 12 having a heel end 14 and a toe end 16. Relative to the ground, as best understood in connection with FIG. 2, sole 12 includes first convexity 18 that performs the function of the bottom of a natural heel, concavity 20 that performs the function of a natural arch, and second convexity 22 that performs the function of the ball of a natural foot.

Sole 12 includes a pair of pylon supports 32, 34 that are separated from one another by slot 36 that is co-extensive with a longitudinal axis of symmetry of foot 10. Slot 36 divides heel end 14 into a lateral heel member 14a and a medial heel member 14b.

Lateral pylon support 32 which forms a part of lateral heel member 14 has a greater thickness and less flexibility than medial pylon support 34 as indicated in FIGS. 1 and 3. Lateral pylon support 32 is also positioned in trailing relation to medial pylon support 34 and said members are therefore hereinafter referred to as lateral, posterior pylon support 32 and medial, anterior pylon support 34.

Tubular pylon connector 40 is secured to the heel side of lateral, posterior pylon support 32, centrally thereof, and tubular pylon connector 42 is secured to the heel side of medial, anterior pylon support 34, centrally thereof. A lateral, posterior pylon, not shown, is received within pylon connector 40 and a medial, anterior pylon, not shown, is received within pylon connector 42 when prosthetic foot 10 is engaged to a prosthetic leg that includes said unillustrated pylons.

The greater thickness and reduced flexibility of lateral pylon support 32 ensures that instabilities appearing on foot 10 will be shifted in a medial direction, just like a natural foot. Slot 36 enables lateral pylon support 32 to respond to instabilities substantially independently of medial pylon support 34, and vice versa.

Lateral, posterior pylon support 32 is a part of lateral heel member 14a and is formed by a gradual ninety degree bend 33 formed in sole 12. Accordingly, said lateral, posterior pylon support 32 is normal to sole 12. Gradual ninety degree bend 33 begins at transverse parting line 44 which begins about mid-length of concavity 20 as depicted in FIG. 2.

Medial, anterior pylon support 34 is a part of medial heel part 14b and is formed by a first return bend 35 having a bight substantially coincident with the trailing end of heel 14 as best understood in connection with FIG. 2. A straight section 39, parallel to sole 12, extends a predetermined distance toward the toe end 16 of foot 10. Straight section 39 terminates in and is formed integrally with a gradual ninety degree upwardly turned bend 41 that forms medial, anterior pylon support 34. The length of straight section 39 is sufficient to position medial, anterior pylon support 34 in leading relation to posterior pylon support 32.

Heel extension 15 is a part of lateral heel member 14a and is formed integrally with the lateral side only of sole 12 and diverges from lateral, posterior pylon support 32 at diverging point 44. Heel extension 15 provides a dynamic response in the horizontal plane during heel strike. This eliminates the bounce caused by the dynamic response in the vertical plane of prior art prosthetic feet.

The merging of lateral, posterior pylon support 32 with sole 12 at transverse parting line 44 about mid-length of arch 20, in cooperation with heel extension 15, eliminates the flat spot of earlier prosthetic feet because such construction provides a smooth transition from heel strike to mid stance to push off.

Moreover, the bifurcated construction of pylon supports 32, 34 and the greater thickness of lateral, posterior pylon support 32 enhances the stability of the user because said greater thickness serves to shift the weight of the user toward the medial side of the foot and thus harnesses the stabilizing power of the sound foot that opposes the prosthetic foot.

Return bend 35 that forms medial heel member 14b enables medial, anterior pylon support 34 to flex or "give" more than lateral, posterior pylon support 32 when a user walks in a normal gait. This structure, together with the greater thickness of lateral, posterior pylon support 32, further ensures that instabilities appearing on the unillustrated prosthetic leg pylons will be shifted primarily from lateral, posterior pylon support 32 to medial, anterior pylon support 34. Such re-distribution of forces enables the healthy opposed leg to become involved in restoring balance when external forces threaten such balance.

Figure 4:
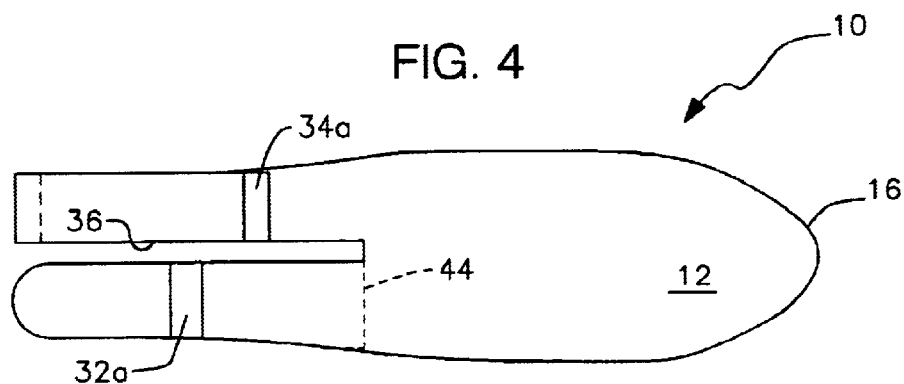
FIG. 4 is a top plan view of a second embodiment of a prosthetic foot with multiple load points having an upper section and sole.
Figure 5:
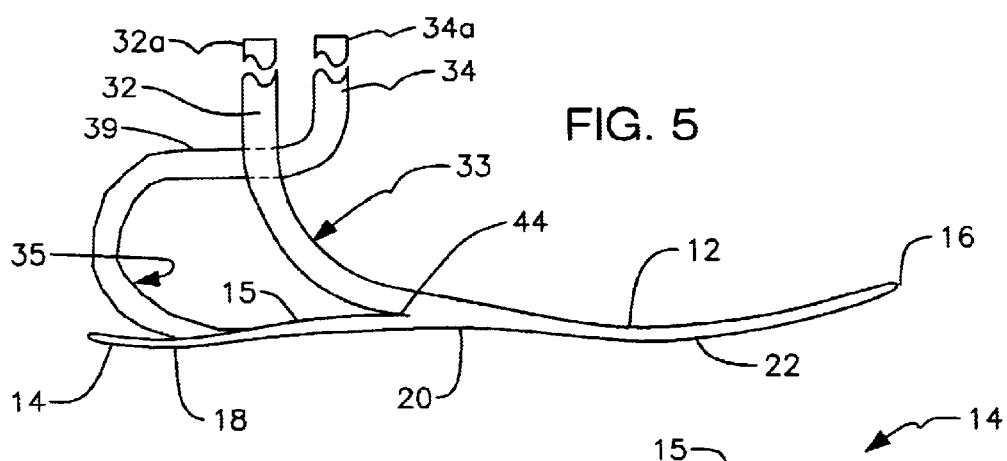
FIG. 5 is a side elevational view of the embodiment of FIG. 4.
Figure 6:
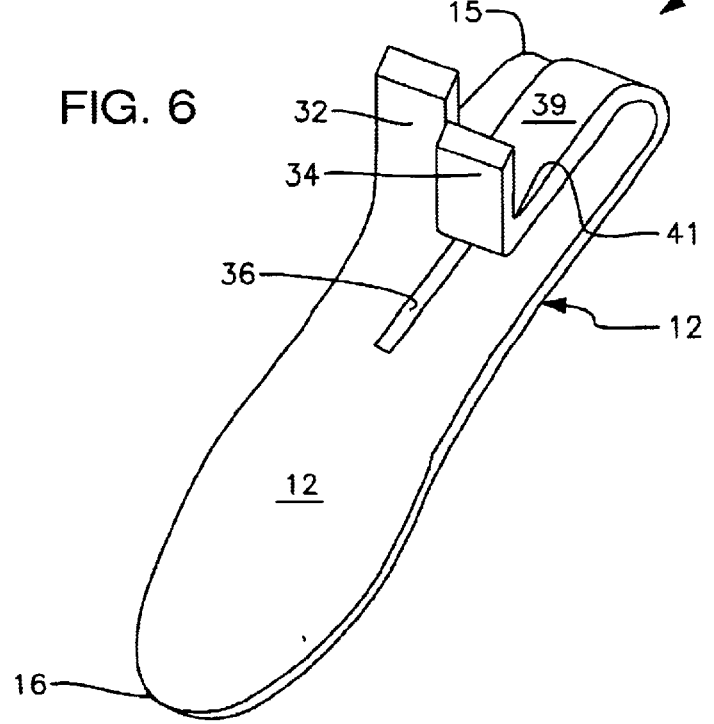
FIG. 6 is a perspective view of the embodiment of FIG. 4.

The second embodiment of novel dynamic prosthetic foot 10 is depicted in FIGS. 4–6. In this embodiment, pylon supports 32, 34 are elongated, thereby becoming pylons 32a, 34a, and pylon connectors 40, 42 are eliminated. Pylons 32a, 34a are about twenty inches (20") in length and are cut to size by a prosthetist at the time prosthetic foot 10 is fitted to a patient.

Figure 7:
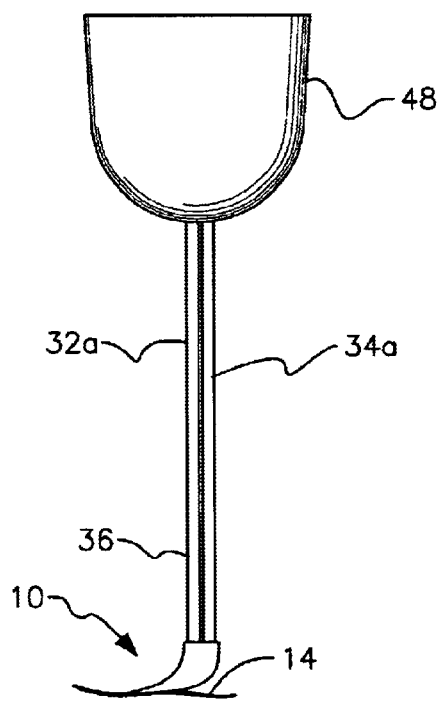
FIG. 7 is a perspective view of the second embodiment when attached to a socket.

FIG. 7 depicts the novel structure when equipped with elongate pylons 32a, 34a.

After pylons 32a, 34a have been cut to a desired length, the prosthetist has several options by which the pylons may be connected to prosthetic socket 48. Pylons 32a, 34a may be laminated into prosthetic socket 48 as illustrated in said FIG. 7. This forms a permanent connection between pylons 32a, 34a and socket 48.

Figure 8:
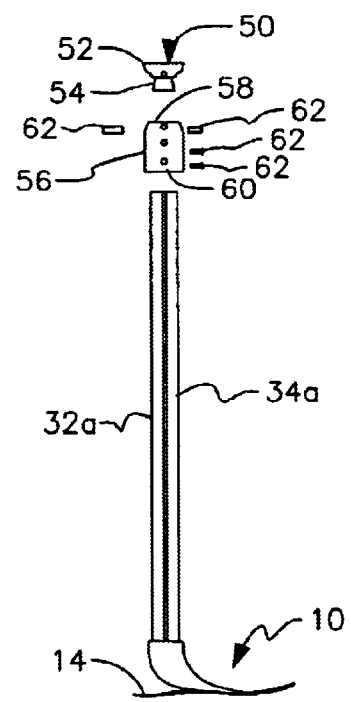
FIG. 8 is a perspective view of the second embodiment and further depicting connector means, in exploded form, for connecting the elongate pylons of said second embodiment to a socket.

A second option includes the use of a commercially available pyramid connector 50 as depicted in FIG. 8. Such pyramid connectors have been in use for fifty or so years. Pyramid connector 50 includes upper part 52 and lower part 54 that depends from the upper part. Upper part 52 is attached to the lowermost or distal end of socket 48. A hollow pyramid-receiving connector 56 has an open upper end 58 that receives lower part 54 of pyramid connector 50 and an open lower end 60 that receives the respective uppermost ends of pylons 32a, 34a. Lower end 54 of pyramid connector 50 and the respective upper ends of pylons 32a, 34a are captured in said hollow pyramid-receiving connector 56 by a plurality of set screws and other suitable fastening means, collectively denoted 62.

Pyramid connector 52 and pyramid-receiving connector 56 are employed to enable adjustment of the angle of pylons 32a, 34a so that prosthetic foot 10 falls in the correct medial/lateral and anterior/posterior planes, as perhaps best understood by making reference to FIG. 8.

A third option available to the prosthetist after cutting pylons 32a, 34a to their correct length is to laminate the pylons to an unillustrated component and to attach that component to the socket.

Figure 9A:
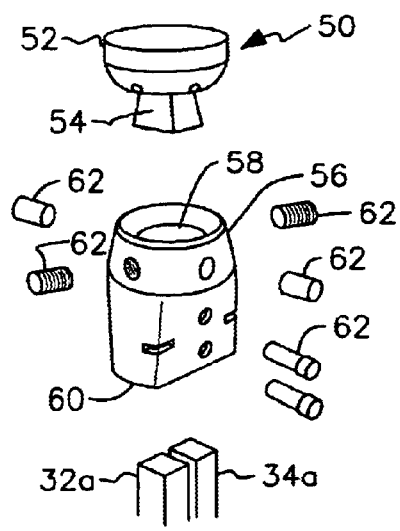
FIG. 9A is an exploded first perspective view of said connector means.
Figure 9B:
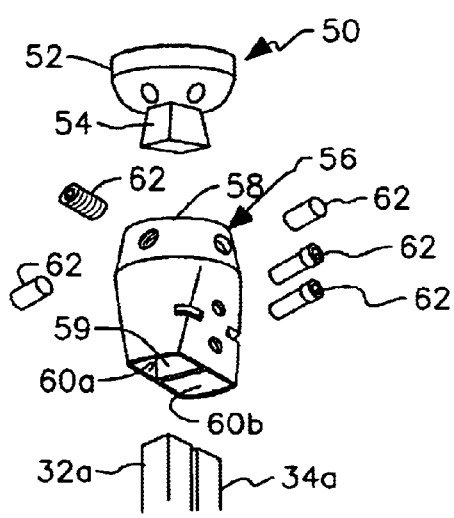
FIG. 9B is an exploded second perspective view of said connector means.
Figure 9C:
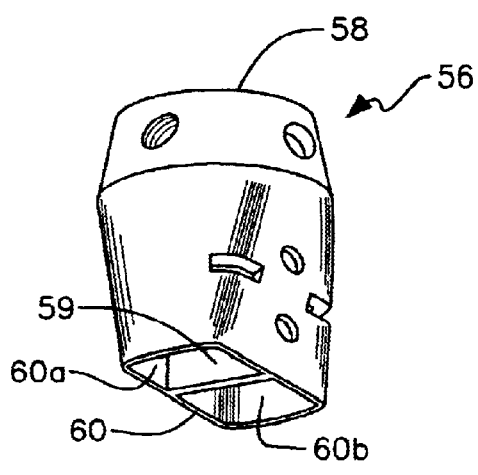
FIG. 9C is a first perspective view of a pyramid-receiving connector.
Figure 9D:
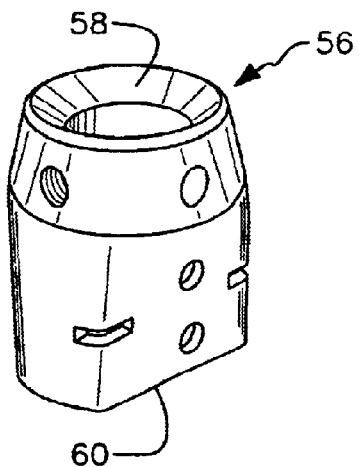
FIG. 9D is a second perspective view of said pyramid-receiving connector.

FIGS. 9A and 9B provide a more detailed perspective view of pyramid connector 50 and pyramid-receiving connector 56. FIGS. 9C and 9D provide a more detailed perspective view of pyramid-receiving connector 56. Partition wall 59 divides open lower end 60 of pyramid-receiving connector 56 into compartments 60a, 60b for receiving pylons 30a, 32a, respectively.

The novel structure enhances the lateral stability, the torsional flex, and the anisotropic stiffness of foot 10.

The reduced torsional stiffness provided by the double pylons of this invention is of major significance. Some torsion in the shin is desirable. More precisely, torsion that can be controlled by the thickness and geometry of the cross section is advantageous over completely rigid pylons. The double pylons of this invention, each of which has a cross section of preselected size, enable the prosthesis user to participate in sporting activities such as golf.

Moreover, the novel foot can flex in the medial plane without having parts that move relative to one another and rub against one another. This represents one of the major breakthroughs of this invention.

Advantageously, heel 14 provides a dynamic response in the horizontal plane during heel strike. This heel elasticity eliminates the vertical bounce caused by the dynamic response in the vertical plane of prior art prosthetic feet. The merging of pylon supports 32, 34 (FIGS. 1–3) or pylons 32a, 34a (FIGS. 4–6) with sole 12 at transverse parting line 44 about mid-length of arch 20 eliminates the flat spot of earlier prosthetic feet because such construction provides a smooth transition from heel strike to push off. Moreover, the bifurcated construction of pylon supports 32, 34 (FIGS. 1–3) or pylons 32a, 34a (FIGS. 4–6) and the greater thickness of lateral pylon support 32 or lateral pylon 32a enhances the stability of the user because said greater thickness serves to shift the weight of the user toward the medial side of the foot and thus harnesses the stabilizing power of the sound foot that opposes the prosthetic foot.

It will thus be seen that the objects set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A dynamic prosthetic foot having multiple load points, comprising:
   a sole having a toe end and a heel end;
   a slot formed in said heel end, said slot substantially coincident with a longitudinal axis of said dynamic prosthetic foot and said slot extending from said heel end of said sole to a preselected point in said sole;
   said slot dividing said heel end into a lateral heel member and a medial heel member;
   said heel end having a pair of pylon supports formed therein, said pylon supports being separated from one another by said slot;
   said pair of pylon supports including a lateral, posterior pylon support and a medial, anterior pylon support;
   a heel extension, forming a part of said lateral heel member, being integral and generally coplanar with a lateral side only of said sole;
   said lateral, posterior pylon support diverging from said heel extension along a preselected transverse line about mid-length of said lateral side of said sole;
   said lateral heel member including a gradual ninety degree bend formed in said sole, said gradual ninety degree bend terminating in a vertical part that forms said lateral, posterior pylon support, said lateral, posterior pylon support being disposed substantially perpendicular to said sole;
   said medial heel member including a return bend formed in said sole at said heel end thereof and said medial heel member including a straight section substantially parallel to said sole that extends toward said toe of said foot;
   said straight section terminating in a gradual ninety degree bend formed integrally with said straight section, said gradual ninety degree bend terminating in a vertical part that forms said medial, anterior pylon support, said medial, anterior pylon support being disposed normal to said sole;
   said straight section having a length sufficient to position said medial, anterior pylon support in leading, anterior relation to said lateral, posterior pylon support;
   a lateral, posterior pylon connector secured to a trailing end of said lateral, posterior pylon support, said lateral, posterior pylon connector adapted to receive a lateral, posterior pylon of a prosthetic leg;
   a medial, anterior pylon connector secured to a trailing end of said medial, anterior pylon support, said lateral, anterior pylon connector adapted to receive a medial, anterior pylon of a prosthetic leg;
   whereby forces acting on said lateral, posterior pylon connector are substantially confined to said lateral, posterior pylon support and forces acting on said medial, anterior pylon connector are substantially confined to said medial, anterior pylon support;
   whereby said heel extension, said lateral, posterior pylon support and said medial, anterior pylon support cooperate with one another to provide a prosthetic foot that facilitates a rolling transition from heel strike to mid stance to push off.

2. The dynamic prosthetic foot of claim 1, wherein said lateral, posterior pylon support has a greater thickness than said medial, anterior pylon support, said greater thickness imparting greater strength and less flexibility so that forces applied to said lateral, posterior pylon support and said medial, anterior pylon support are transferred more to said medial, anterior pylon support than to said lateral, posterior pylon support, thereby mimicking the reaction of a natural foot to forces applied thereto.

3. The dynamic prosthetic foot of claim 1, wherein said sole has a first convexity formed in said heel end that performs the function of the bottom of a natural heel.

4. The dynamic prosthetic foot of claim 3, wherein said sole has a concavity longitudinally spaced from said first convexity, said concavity performing the function of a natural arch.

5. The dynamic prosthetic foot of claim 4, wherein said sole has a second convexity longitudinally spaced from said concavity, said second convexity performing the function of the ball of a natural foot.

6. A dynamic prosthetic foot having multiple load points, comprising:
   a sole having a toe end and a heel end;
   a slot formed in said heel end, said slot substantially coincident with a longitudinal axis of said dynamic prosthetic foot and said slot extending from said heel end of said sole to a preselected point in said sole;
   said slot dividing said heel end into a lateral heel member and a medial heel member;
   said heel end having a pair of elongate pylons formed therein, said elongate pylons being separated from one another by said slot;
   said pair of elongate pylons including a lateral, posterior elongate pylon and a medial, anterior elongate pylon;
   a heel extension, forming a part of said lateral heel member, being integral with a lateral side only of said sole;
   said lateral, posterior elongate pylon diverging from said heel extension along a preselected transverse line about mid-length of said lateral side of said sole;
   said lateral heel member including a gradual ninety degree bend formed in said sole, said gradual ninety degree bend terminating in a vertical part that forms said lateral, posterior elongate pylon, said lateral, posterior elongate pylon being disposed substantially perpendicular to said sole;
   said medial heel member including a return bend formed in said sole at said heel end thereof and said medial heel member including a straight section substantially parallel to said sole that extends toward said toe of said foot;

said straight section terminating in a gradual ninety degree bend formed integrally with said straight section, said gradual ninety degree bend terminating in a vertical part that forms said medial, anterior elongate pylon, said medial, anterior elongate pylon being disposed normal to said sole;

said straight section having a length sufficient to position said medial, anterior elongate pylon in leading, anterior relation to said lateral, posterior elongate pylon;

whereby forces acting on said lateral, posterior elongate pylon are substantially confined to said lateral, posterior elongate pylon and forces acting on said medial, anterior elongate pylon are substantially confined to said medial, anterior elongate pylon;

whereby said heel extension, said lateral, posterior elongate pylon and said medial, anterior elongate pylon cooperate with one another to provide a prosthetic foot that facilitates a rolling transition from heel strike to mid stance to push off.

7. The dynamic prosthetic foot of claim 6, wherein said lateral, posterior elongate pylon has a greater thickness than said medial, anterior elongate pylon, said greater thickness imparting greater strength and less flexibility so that forces applied to said lateral, posterior elongate pylon and said medial, anterior elongate pylon are transferred more to said medial, anterior elongate pylon than to said lateral, posterior elongate pylon, thereby mimicking the reaction of a natural foot to forces applied thereto.

8. The dynamic prosthetic foot of claim 6, wherein said sole has a first convexity formed in said heel end that performs the function of the bottom of a natural heel.

9. The dynamic prosthetic foot of claim 8, wherein said sole has a concavity longitudinally spaced from said first convexity, said concavity performing the function of a natural arch.

10. The dynamic prosthetic foot of claim 9, wherein said sole has a second convexity longitudinally spaced from said concavity, said second convexity performing the function of the ball of a natural foot.

11. The dynamic prosthetic foot of claim 6, wherein said lateral and medial pylons are laminated at respective uppermost ends thereof to a prosthetic socket.

12. The dynamic prosthetic foot of claim 6, wherein said lateral and medial pylons are connected at respective uppermost ends thereof to a connector member and wherein said connector member is laminated to a prosthetic socket.

13. The dynamic prosthetic foot of claim 6, wherein said lateral and medial pylons are connected at respective uppermost ends thereof to a pyramid-receiving connector that engages a pyramid that depends from a prosthetic socket.

* * * * *